US012239402B2

(12) United States Patent
Waterbury et al.

(10) Patent No.: US 12,239,402 B2
(45) Date of Patent: Mar. 4, 2025

(54) ROTATABLE CARRIAGE FOR AN INSTRUMENT HOLDER

(71) Applicant: INTUITIVE SURGICAL OPERATIONS, INC., Sunnyvale, CA (US)

(72) Inventors: Andrew Cullen Waterbury, Santa Clara, CA (US); Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 720 days.

(21) Appl. No.: 17/444,162

(22) Filed: Jul. 30, 2021

(65) Prior Publication Data

US 2022/0039890 A1 Feb. 10, 2022

Related U.S. Application Data

(60) Provisional application No. 63/063,186, filed on Aug. 7, 2020.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/70* (2016.02); *A61B 46/10* (2016.02); *B25J 5/00* (2013.01);
(Continued)

(58) Field of Classification Search
CPC ......... A61B 34/35; A61B 34/37; A61B 34/70; A61B 46/10; A61B 2017/00477;
(Continued)

(56) References Cited

U.S. PATENT DOCUMENTS 11,696,227 B2 * 7/2023 Palamara .............. H04W 76/10
370/338
11,969,227 B2 * 4/2024 Rohr Daniel .......... A61B 34/30
(Continued)

FOREIGN PATENT DOCUMENTS

WO WO-2018145100 A1 * 8/2018 ......... A61B 1/00128

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Tan-Uyen T Ho
*Assistant Examiner* — Cherie M Poland
(74) *Attorney, Agent, or Firm* — JONES ROBB, PLLC

(57) ABSTRACT

An instrument holder generally includes a carriage rotatable with respect to a carriage support, a light pipe extending axially through the carriage, and an electrical conductor extending through the carriage radially outward of the light pipe. The light pipe can transmit light energy and the electrical conductor can transmit electricity between a proximal end portion and a distal end portion of the carriage to a medical instrument. The rotatable carriage may include a sterile adapter assembly positioned at the proximal and/or distal end portions of the rotatable carriage. The sterile adapter assembly may include a roll disk rotatable with respect to the outer frame, an inner disk rotatable with respect to the roll disk, and a light pipe to transmit light energy through the roll disk. The inner disk can transfer movement of an actuator between the rotatable carriage and the instrument.

14 Claims, 11 Drawing Sheets

(51) Int. Cl.
*A61B 46/10* (2016.01)
*B25J 5/00* (2006.01)
*B25J 19/00* (2006.01)

(52) U.S. Cl.
CPC ....... *B25J 19/0037* (2013.01); *B25J 19/0041* (2013.01)

(58) Field of Classification Search
CPC .............. A61B 2018/00178; B25J 5/00; B25J 19/0037; B25J 19/0041; G06N 20/00; H04N 1/60; B22F 12/30; B33Y 10/00; H01F 27/2804; H01F 41/041; H02J 50/005
See application file for complete search history.

(56) References Cited

U.S. PATENT DOCUMENTS

| | | | |
|---|---|---|---|
| 12,004,832 B2 * | 6/2024 | Waterbury | A61B 34/37 |
| 2003/0055409 A1 * | 3/2003 | Brock | A61B 5/416 |
| | | | 606/1 |
| 2011/0282358 A1 * | 11/2011 | Gomez | A61B 34/00 |
| | | | 606/130 |
| 2015/0090057 A1 * | 4/2015 | Pacheco | F16H 19/02 |
| | | | 74/25 |
| 2017/0072561 A1 * | 3/2017 | Schlegel | A61B 34/30 |
| 2022/0008152 A1 * | 1/2022 | Rohr Daniel | A61B 90/37 |
| 2022/0039892 A1 * | 2/2022 | Waterbury | A61B 34/37 |

* cited by examiner

ROTATABLE CARRIAGE FOR AN INSTRUMENT HOLDER

CROSS REFERENCE TO RELATED APPLICATION

This application claims the benefit under 35 U.S.C. § 119(e) of U.S. Provisional Application No. 63/063,186, filed Aug. 7, 2020, entitled "Rotatable Carriage For An Instrument Holder," which is hereby incorporated by reference for all purposes in its entirety.

TECHNICAL FIELD

Aspects of the present disclosure generally relate to devices and methods for performing a computer-assisted teleoperated procedure and, more specifically, to devices for transferring degrees of freedom to a tool.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. An operator (e.g., a physician) may insert minimally invasive medical instruments (surgical, diagnostic, therapeutic, biopsy instruments, etc.) through these natural orifices or incisions to reach a target tissue location. Robotic medical systems allow a user to control such medical instruments via a manipulator to which the instrument is mounted. One such minimally invasive technique is to move one or more instruments to a region of interest within the patient anatomy to perform a medical procedure. Control of such a manipulator assembly by an operator involves the management of several degrees of freedom including at least the management of insertion, retraction, and roll of the instrument with respect to the patient anatomy, as well as articulation of an instrument end effector.

Minimally invasive telesurgical systems allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments.

Communication signals may be transmitted between components of a robotic medical system using various cables, including optical fibers, coaxial conductors, copper conductors, twisted wire pairs, etc. When using such communication cables on articulating medical instruments, it is desirable to reduce stress and friction on the internal components of the cable to extend the cable life. Twisting a wrapped cable can impart an unwrap torque, causing a tensile load on the inner wrap and/or core of the cable and significantly reduce cable life. Loading of the cable and articulation of the end effector can further contribute to the unwrap torque. Internal friction of the cable at different twisted states can adversely affect the consistency of movement of the medical instrument during use.

SUMMARY

In accordance with embodiments of the present disclosure, an apparatus is provided. The apparatus generally includes a carriage rotatable with respect to a carriage support, a light pipe extending axially through the carriage and configured to transmit light energy between a proximal end portion and a distal end portion of the carriage, and electrical conductors extending through the carriage radially outward of the light pipe. The electrical conductors of the apparatus may be configured to transmit electricity between the proximal end portion and the distal end portion of the carriage.

In accordance with embodiments of the present disclosure, a sterile adapter assembly configured for use with a rotatable carriage is provided. The sterile adapter assembly generally includes in instrument holder base member with a longitudinally slidable carriage and a sterile adapter. The sterile adapter generally includes a fixed frame couplable to the slidable carriage, a roll disk positioned within the frame and rotatable with respect to the frame, an inner disk positioned within the roll disk and rotatable with respect to the roll disk, and a light pipe positioned in the roll disk that may be configured to transmit light energy through the roll disk. The inner disk may be further configured to transfer movement of an actuator.

In accordance with any of the embodiments disclosed herein, the apparatus may further include an alignment projection extending outwardly from one of the distal end portion of the carriage and the proximal end portion of the medical instrument, and an alignment recess extending into the other of the distal end portion of the carriage and the proximal end portion of the medical instrument. The alignment projection may have a shape corresponding to a shape of the alignment recess to bring the carriage and the medical instrument into alignment in a lateral direction.

In accordance with any of the embodiments disclosed herein, the apparatus may further include a clocking projection extending outwardly from the alignment projection, and a clocking recess extending into the alignment recess. The clocking projection may have a shape corresponding to a shape of the clocking recess to orient the medical instrument and the carriage into a clocked position.

In accordance with any of the embodiments disclosed herein, the inner disk may further include a plurality of separate, non-overlapping disks positioned at different points on the roll disk and may be configured to transfer movement of a plurality of actuators.

In accordance with any of the embodiments disclosed herein, the inner disk may be a first inner disk, and the sterile adapter may further include a second inner disk positioned within the first inner disk and configured to transfer the movement of an actuator. The light pipe may be positioned on the second inner disk.

In accordance with any of the embodiments disclosed herein, the sterile adapter assembly may further include an alignment projection extending outwardly from one of the slidable carriage and the sterile adapter, and an alignment recess extending into the other of the slidable carriage and the sterile adapter. The alignment projection may have a shape corresponding to a shape of the alignment recess to bring the slidable carriage and the sterile adapter into alignment.

In accordance with any of the embodiments disclosed herein, the sterile adapter assembly may further include a clocking projection extending outwardly from the alignment projection, and a clocking recess extending into the alignment recess. The clocking projection may have a shape corresponding to a shape of the clocking recess to orient a medical instrument and the carriage into a clocked position.

In accordance with any of the embodiments disclosed herein, the apparatus may further include a drape coupled to a distal or proximal sterile adapter and configured to maintain a sterile barrier during a surgical procedure.

In accordance with any of the embodiments disclosed herein, the sterile adapter may further include a catch projecting axially away from the distal end portion of the carriage. The catch may have a catch protrusion configured to limit the axial separation distance of the instrument from the carriage.

In accordance with any of the embodiments disclosed herein, the proximal sterile adapter may be positioned at the proximal end portion of the carriage. The proximal sterile adapter may be configured to transmit mechanical movement, light energy, and/or electricity between a connector and the carriage.

DESCRIPTION OF THE DRAWINGS

Many aspects of the present disclosure can be better understood with reference to the detailed description along with the following drawings. The components in the drawings are not necessarily drawn to scale. Instead, emphasis is placed on illustrating clearly the principles of the present disclosure. Furthermore, components can be shown as transparent in certain views for clarity of illustration only and not to indicate that the component is necessarily transparent. Components may also be shown schematically.

In the specification, it should be appreciated that like reference numerals are used to identify like elements illustrated in one or more of the figures for purposes of illustrating embodiments of the present disclosure and not for purposes of limiting the same.

DETAILED DESCRIPTION

The present disclosure generally relates to an instrument holder for a robotic medical system, the instrument holder having a rotatable carriage for carrying a medical instrument. The systems described herein are designed to extend instrument cable life by rotating the rotatable carriage to roll the medical instrument, rather than rotating the shaft of the instrument relative to other components of the instrument. Various medical systems may include communication cables on one or more modular medical instruments. Embodiments of the present disclosure reduce stress and friction on the internal components of the instrument and instrument cable to extend the cable life. Using a rotatable carriage to roll the medical instrument can minimize unwrap torque on the instrument cable, reducing tensile load on the inner wrap and/or core of the cable. By rolling the rotatable carriage, the internal loading of the cable is essentially uniform. Additionally, the cable tension is more consistent, making the drivetrain friction more consistent such that movement of the medical instrument during use can be more precise. During installation and removal of the medical instrument to and from the rotatable carriage, it may be desirable to limit the insertion of the medical instrument through the cannula, as unintended and/or excessive insertion can cause injury to the patient and/or damage to the equipment of the system. It may be further desirable to align and clock the medical instrument with respect to the rotatable carriage during installation.

The present disclosure describes various instruments and portions of instruments in terms of their state in three-dimensional space. As used herein, the term position refers to the location of an object or a portion of an object in a three-dimensional space (e.g., three degrees of translational freedom along Cartesian X-, Y-, and Z-coordinates). As used herein, the term orientation refers to the rotational placement of an object or a portion of an object (e.g., three degrees of rotational freedom, such as roll, pitch, and yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object. Further, as used herein, the term "distal" means a location closer to a surgical site and the term "proximal" means a location farther away from the surgical site, unless otherwise indicated.

Figure 1A:
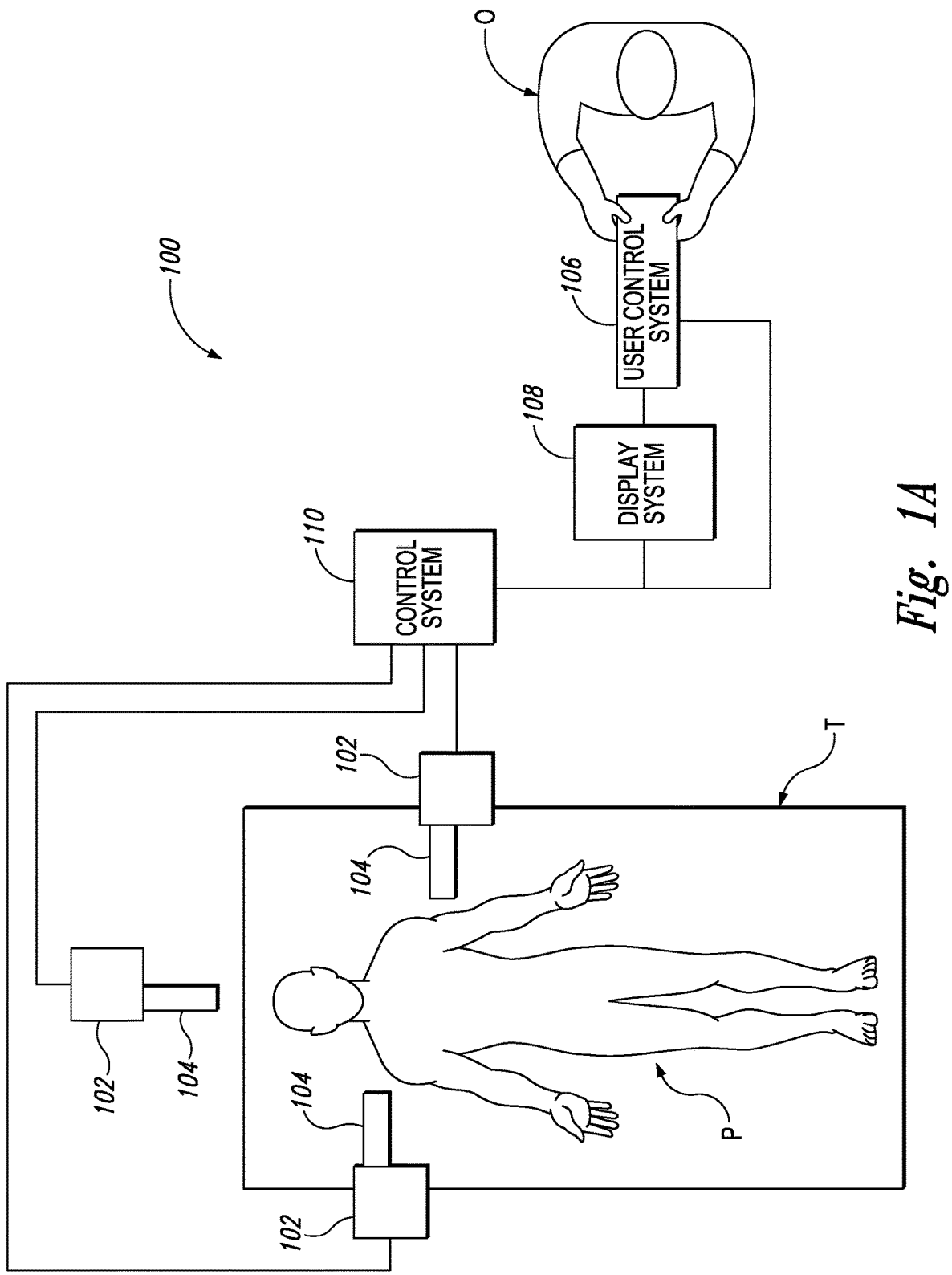
FIG. 1A is a simplified diagram of a medical system configured in accordance with an embodiment of the present disclosure.

FIG. 1A is a simplified diagram of a medical system 100 ("system 100"). In some embodiments, the system 100 may be suitable for use in, for example, surgical, teleoperated surgical, diagnostic, therapeutic, or biopsy procedures. While some embodiments are provided herein with respect to such procedures, any reference to medical or surgical instruments and medical or surgical methods is intended as non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

As shown in FIG. 1A, the system 100 generally includes a plurality of manipulator assemblies 102 (having one or more drive elements). Although three manipulator assemblies 102 are illustrated in the embodiment of FIG. 1A, in other embodiments, more or fewer manipulator assemblies may be used. The exact number of manipulator assemblies will depend on the medical procedure and the space constraints within the operating room, among other factors. Multiple user control systems 106 may be co-located or they may be positioned in separate locations. Multiple user control systems 106 allow more than one operator to control one or more teleoperated manipulator assemblies in various combinations.

The manipulator assembly 102 is used to operate a medical instrument 104 (e.g., a surgical instrument or an image capturing device) in performing various procedures on a patient P. The medical instrument 104 may be sterile prior to being used in the various procedures. The manipulator assembly 102 may be teleoperated, non-teleoperated, or a hybrid teleoperated and non-teleoperated assembly with select degrees of freedom of motion that may be motorized and/or teleoperated, and select degrees of freedom of motion that may be non-motorized and/or non-teleoperated. In some embodiments, the manipulator assembly 102 may be mounted near an operating or surgical table T, or the manipulator assembly 102 may be mounted directly to the table T or to a rail coupled to the table T. In various other embodiments, the manipulator assembly 102 may be mounted to a manipulating system (e.g., a patient-side cart). The manipulating system may be separate from and spaced from the table T in the operating room and may be independently movable relative to the table T.

The manipulator assembly 102 may be mounted to a ceiling, floor, and/or wall of the operating room. In embodiments in which a plurality of manipulator assemblies 102 are employed, one or more of the manipulator assemblies 102 may support surgical instruments, and another of the manipulator assemblies may support an image capturing device such as a monoscopic or stereoscopic endoscope. In such embodiments, one or more of the manipulator assemblies 102 may be mounted to any structure or in any manner as described above. For example, one manipulator assembly 102 may be mounted to the table T and another manipulator assembly 102 may be mounted to a manipulating system.

A user control system 106 allows an operator (e.g., a surgeon or other clinician, as illustrated in FIG. 1A) to view the interventional site and to control the manipulator assembly 102. In some examples, the user control system 106 is a surgeon console, which can be located in the same room as the operating or surgical table T, such as at the side of a table on which the patient P is located. However, the operator can be located in a different room or a completely different building from patient P. The user control system 106 generally includes one or more input devices for controlling the manipulator assembly 102. The input devices may include any number of a variety of devices, such as joysticks, trackballs, data gloves, trigger-guns, hand-operated controllers, voice recognition devices, body motion or presence sensors, and/or the like. The input devices may be provided with the same degrees of freedom as the associated medical instrument 104 to provide the operator O a strong sense of directly controlling the medical instrument 104. In this regard, the input devices may provide the operator O with telepresence: the perception that the input devices are integral with medical instrument 104.

The input devices may have more or fewer degrees of freedom than the associated medical instrument 104 and still provide the operator O with telepresence. The input devices may optionally be manual input devices that move with six degrees of freedom, and may also include an actuatable handle for actuating instruments (for example, for closing grasping jaws, applying an electrical potential to an electrode, delivering a medicinal treatment, etc.).

The manipulator assembly 102 may support the medical instrument 104 and may include a kinematic structure of one or more non-servo controlled links (e.g., a manipulator support structure having one or more links that are manually positioned and locked in place), and/or one or more servo controlled links (e.g., one or more links that are controlled in response to commands from a control system), and an instrument holder. The manipulator assembly 102 may optionally include a plurality of actuators or motors that drive inputs on the medical instrument 104 in response to commands from the control system (e.g., a control system 110). The actuators may optionally include drive systems that when coupled to the medical instrument 104 may advance the medical instrument 104 into a naturally or surgically created anatomic orifice.

Other drive systems may move the distal end of the medical instrument 104 in multiple degrees of freedom, which can include three degrees of linear motion (e.g., linear motion along the X, Y, Z Cartesian axes), and three degrees of rotational motion (e.g., rotation about the X, Y, Z Cartesian axes). Additionally, the actuators can be used to actuate an articulable end effector of the medical instrument 104, e.g., for grasping tissue in the jaws of a biopsy device. Actuator position sensors such as resolvers, encoders, potentiometers, and other mechanisms may provide sensor data to the system 100 describing the rotation and orientation of the shafts of the actuator. Such position sensor data may be used to determine motion of the objects manipulated by the actuators. The manipulator assembly 102 may position its held instrument such that a pivot point occurs at the entry aperture into the patient. The manipulator assembly 102 may then manipulate its held instrument so that the instrument may be pivoted about the pivot point, inserted into and retracted out of the entry aperture, and/or rotated about its shaft axis.

The system 100 may also include a display system 108 for displaying an image or representation of the surgical site and the medical instrument 104. The display system 108 and the user control system 106 may be oriented so the operator O can control the medical instrument 104 and the user control system 106 with the perception of telepresence. The medical instrument 104 may include a visualization system, which may include a viewing scope assembly that records a concurrent or real-time image of a surgical site and provides the image to the operator O and/or other operators or personnel through one or more displays of the system 100, such as one or more displays of the display system 108. The concurrent image may be, for example, a two- or three-dimensional image captured by an endoscope positioned within the surgical site. The visualization system may be implemented as hardware, firmware, software, or a combination thereof that interact with or are otherwise executed by one or more computer processors that may include the processors of the control system 110. The display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images, and/or as images from models created from the pre-operative or intra-operative image data sets.

The system 100 may also include the control system 110. The control system 110 may include at least one memory (not shown) and at least one computer processor (not shown) for effecting control between the medical instrument 104, the user control system 106, and the display system 108. The control system 110 also includes programmed instructions (e.g., a non-transitory machine-readable medium storing the instructions) to implement some or all the methods described in accordance with aspects of the present disclosure disclosed herein, including instructions for providing information to the display system 108. While the control system 110 is shown as a single block in the simplified schematic of FIG. 1A, the system may include two or more data processing circuits with one portion of the processing optionally being performed on or adjacent to the manipulator assembly 102, another portion of the processing being performed at the user control system 106, etc. The processors of the control system 110 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, the control system 110 supports wireless communication protocols such as Bluetooth, IrDA, HomeRF, IEEE 802.11, DECT, and Wireless Telemetry.

Movement of the manipulator assembly 102 may be controlled by the control system 110 such that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, the risk of excessive lateral motion of the shaft that might potentially cause hazardous forces on the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions, or may in part or in full be imposed using data processing and control techniques. In some embodiments, the control system 110 may receive force and/or torque feedback from the medical instrument 104. Responsive to the feedback, the control system 110 may transmit signals to the user control system 106. In some examples, the control system 110 may transmit signals instructing one or more actuators of the manipulator assembly 102 to move the medical instrument 104.

Figure 1B:
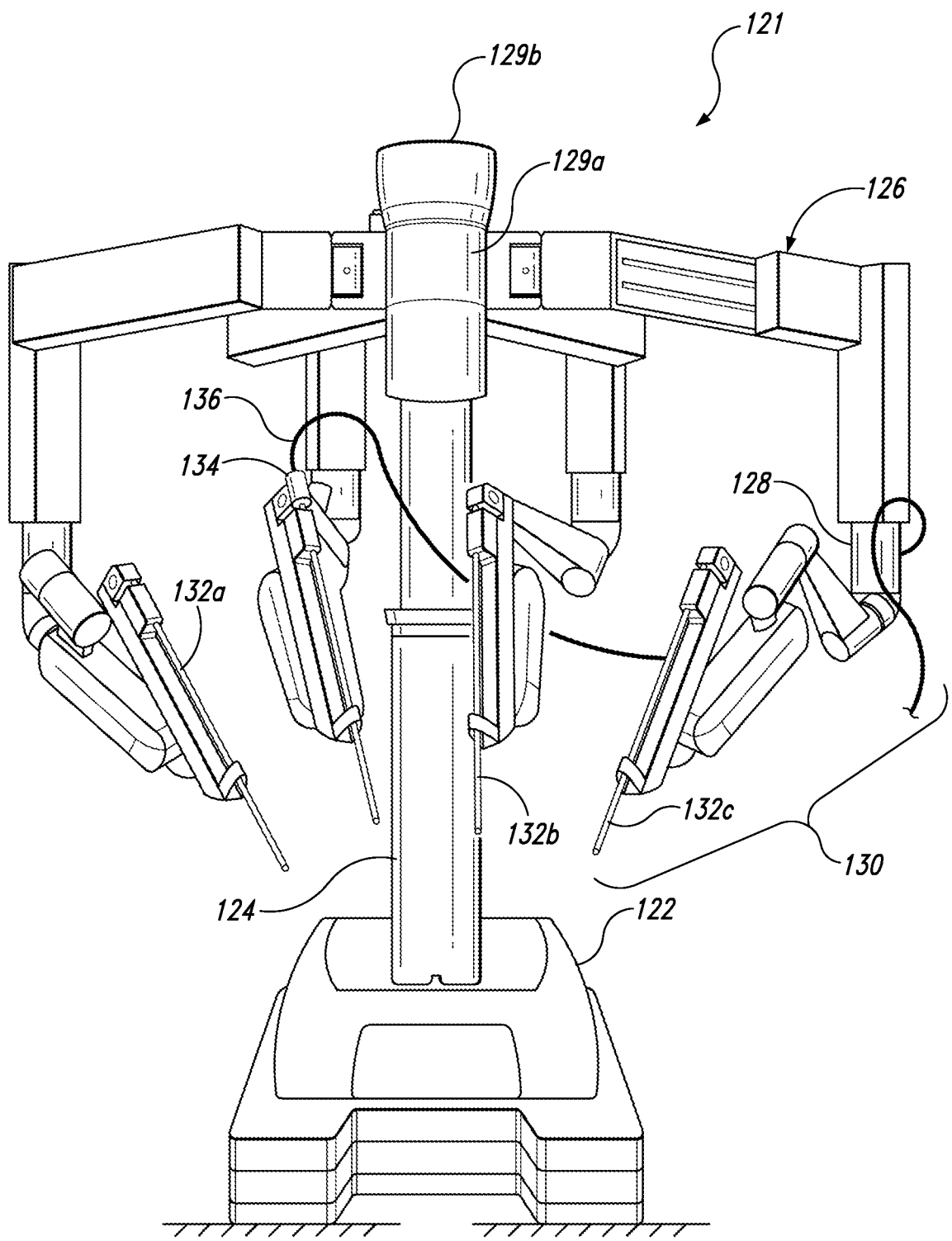
FIG. 1B is a perspective view of a structural representation of the medical system of FIG. 1A.

FIG. 1B is a perspective view of one embodiment of a manipulating system 121 configured in the form of a cart that is located near the patient during a medical procedure. The teleoperational assembly of FIG. 1B may also be referred to as a patient side cart. The manipulating system 121 generally allows manipulation of three medical instruments 132a, 132b, 132c (e.g., the medical instrument 104 of FIG. 1A), and a medical tool 134 that may include an imaging device, such as a stereoscopic endoscope used for the capture of images of the work piece or of the site of the procedure (a "work site"). The medical tool 134 may transmit signals over a cable 136 to a control system (e.g., the control system 110 of FIG. 1A). Manipulation may be provided by robotic manipulators 126 having a number of links that are coupled together and manipulated through joints and a manipulator arm portion 130. The medical instruments 132a, 132b, and 132c, and the medical tool 134 can be positioned and manipulated through natural orifices or incisions in the patient so that a kinematic remote center is maintained at the incisions or natural orifices. Images of the work site can include images of the distal ends of the medical instruments 132a, 132b, and 132c when they are positioned within the field-of-view of the medical tool 134.

The manipulating system 121 may include a drivable base 122 connected to a telescoping column 124, and one or more manipulator assemblies 126. The manipulator assemblies 126 may include a rotating joint 128 that both rotates and translates parallel to the column 124. The manipulator assemblies 126 may be connected to an orienting platform 129a. The orienting platform 129a may be capable of 360 degrees of rotation. The manipulating system 121 may also include a telescoping horizontal cantilever 129b for moving the orienting platform 129a in a horizontal direction.

In the illustrated embodiment, each of the manipulator assemblies 126 includes a manipulator arm portion 130 that may connect directly to the medical instruments 132a, 132b, and 132c and/or the medical tool 134. The manipulator arm portion 130 may be teleoperatable. The manipulator assemblies 126 may include a manipulator support structure that connects the manipulator arm portion 130 to the orienting platform 129a. Optionally, in some embodiments, the manipulator support structure is not teleoperatable, such that the manipulator support structure may be positioned as desired before the operator O begins operation with the teleoperative components.

Figure 2A:
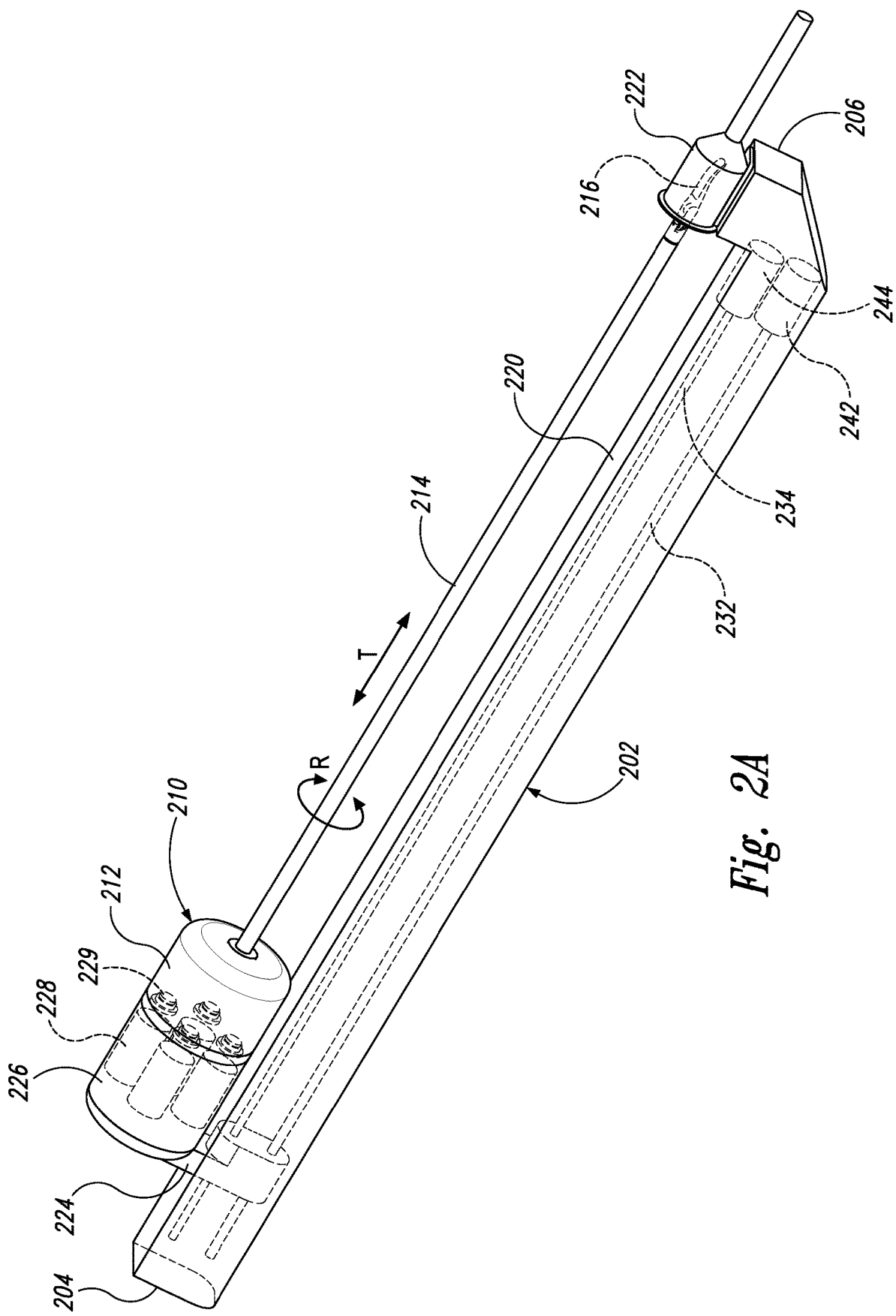
FIGS. 2A and 2B are perspective and right side elevation views, respectively, of an instrument holder and medical instrument configured in accordance with embodiments of the present disclosure.
Figure 2B:
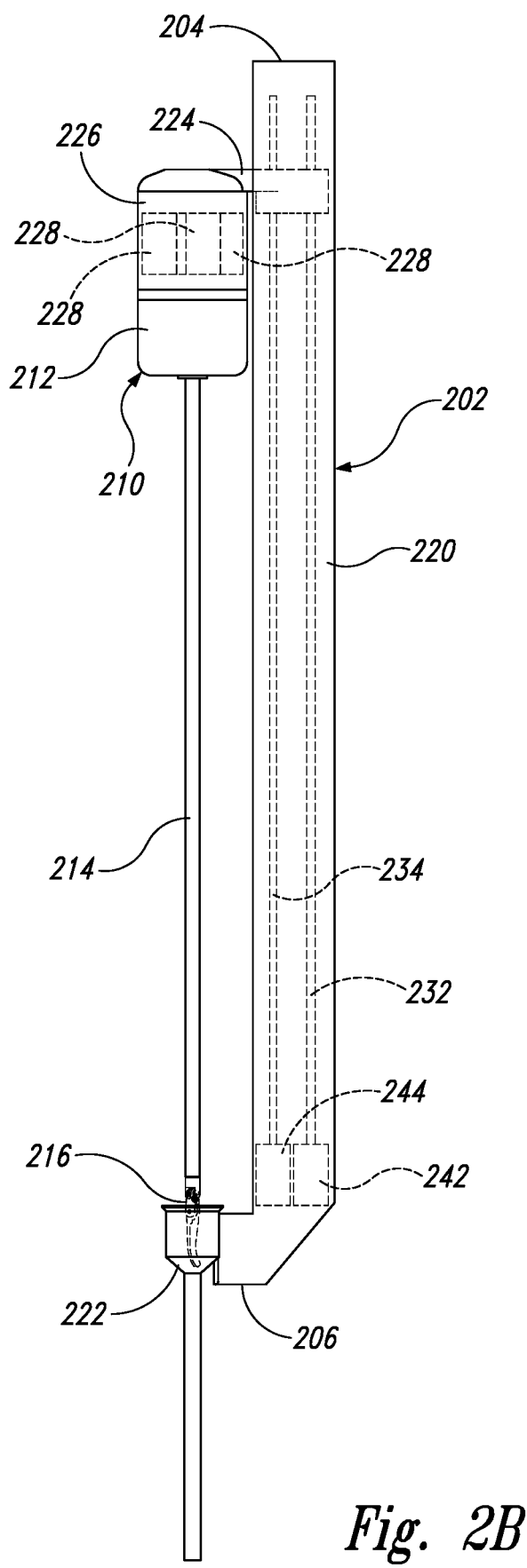

FIGS. 2A and 2B are perspective and right side elevation views, respectively, of an instrument holder 202 and a medical instrument 210 configured in accordance with embodiments of the present disclosure. In some configurations, such as the configuration shown in FIG. 1B, the instrument holder 202 may form part of the manipulator arm portion 130. The medical instrument 210 is generally removably couplable to the instrument holder 202, as will be described in greater detail below. During use, manipulation of the manipulator assemblies 126 can position the instrument holder 202 and medical instrument 210, while the medical instrument 210 is translated, rotated, and/or articulated. The instrument holder 202 may be configured to support and actuate the medical instrument 210 during the medical procedure. As described in further detail below, in some embodiments, a sterile drape may be provided to drape the instrument holder 202 and an associated manipulator assembly 126 (see FIGS. 6A-6E). The sterile drape may be used to maintain a sterile barrier during a surgical procedure and, via a sterile adapter, provide an interface for a medical instrument 210 mounted to the instrument holder 202. The sterile adapter allows for mechanical and electrical signals and energy to be transferred between a non-sterile manipulator assembly 126 and a medical instrument 210 positioned in the sterile field.

The medical instrument 210 may be a therapeutic surgical instrument, an endoscopic camera, etc. Referring to FIGS. 1A-2B together, the instrument holder 202 and the medical instrument 210 may be controlled using the control system 110 such that the operator O can manipulate the medical instrument 210 during a medical procedure using the user control system 106. The instrument holder 202 and the medical instrument 210 may communicate with the system 100 via various cables and connectors suitable for transferring information (e.g., data signals, light, electrical current, etc.) between them and the system 100 through the control system 110. During a procedure, one or more medical instruments 210 can be positioned in the patient coordinate space 120 in relation to the patient P by mounting the medical instruments 210 to other manipulating systems.

The instrument holder 202 may include an instrument holder base member 220 (which may be an elongate spar) having a proximal end portion 204 and a distal end portion 206. The instrument holder base member 220 may be configured to carry and/or position components of the instrument holder 202 during use of the medical instrument 210, and may include one or more surfaces coupled to more proximal portions of the manipulator arm portion 130 (e.g., via one or more joints). In this regard, the instrument holder base member 220 may have a generally constant cross-section along its length such that the instrument holder 202 may be coupled to a manipulator assembly near a central portion of instrument holder 202, or nearer the proximal end portion 204 or the distal end portion 206. In other embodiments, the instrument holder base member 220 has any suitable cross section along its length, and may include one or more features to assist in positioning the instrument holder 202 with respect to the patient coordinate space (e.g., distance indices, protrusions (not shown), indentations (not shown), etc.). The instrument holder base member 220 may have chambers or internal openings to house components of the instrument holder 202, as will be described in greater detail below. The instrument holder base member 220 may be configured to retain a cannula 222 near the distal end portion 206 for providing an interface between the surgical opening in the patient P and the medical instrument 210 during the medical procedure. The cannula 222 may be removably coupled to the instrument holder base member 220 such that the cannula 222 can be separated from the instrument holder base member 220, e.g., for sterilization.

The instrument holder 202 may further include a carriage support 224 that supports and connects a rotatable carriage 226 to the instrument holder base member 220. The carriage support 224 may be slidingly associated with instrument holder base member 220 to translate the rotatable carriage 226 along the instrument holder base member 220 (e.g., longitudinally). The carriage support 224 may include a portion extending into the instrument holder base member 220 to interface with one or more drive elements configured to control an axial position of the carriage support 224 and the rotatable carriage 226 with respect to the instrument holder base member 220, and/or an angular position of the rotatable carriage 226 with respect to the carriage support 224 and the instrument holder base member 220. As shown, the instrument holder 202 may include an axial drive element 242 (e.g., a motor, actuator, etc.) operably coupled to an axial drive shaft 232 to control the axial position of the rotatable carriage 226 with respect to the instrument holder base member 220. The instrument holder 202 may also include a rotational drive element 244 (e.g., a motor, actuator, etc.) operably coupled to a rotational drive shaft 234 to control the axial position of the rotatable carriage 226 with respect to the instrument holder base member 220. The axial and rotational drive shafts 232 and 234 may extend from the axial and rotational drive elements 242 and 244 to the carriage support 224 for axial positioning of the carriage support 224 and the rotatable carriage 226 with respect to the instrument holder base member 220, and angular positioning of the rotatable carriage 226 with respect to the carriage support 224 and the instrument holder base member 220. The axial and rotational drive shafts 232 and 234 are examples of transmission members that may be used to effectuate axial and/or rotational movement of the rotatable carriage 226. In alternative embodiments, the transmission members controlling the axial and/or angular position of the rotatable carriage 226 may include cables, belts, or any other suitable transmission member.

In the illustrated configuration of FIGS. 2A and 2B, the axial drive shaft 232 may have threads (not shown) configured to interface with complementary threads (not shown) in the carriage support 224 such that when the axial drive shaft 232 is rotated, the carriage support 224 traverses along (e.g., longitudinally) the instrument holder base member 220 to a different axial position. When a tool is mounted to the carriage 226 and the carriage 226 is translated longitudinally relative to the instrument holder base member 220 in the direction of arrow T, the instrument shaft and end effector will translate in the direction of arrow T along with the carriage (corresponding to the instrument shaft insertion direction). The rotational drive shaft 234 may have features (e.g., gear teeth and splines) to actuate complementary features of the carriage support 224 and/or rotatable carriage 226 such that when the rotational drive shaft 234 is rotated, the rotatable carriage 226 rotates correspondingly with respect to the carriage support 224. When a tool is mounted to the carriage 226 and the carriage is rotated relative to the instrument holder base member 220 in the direction of arrow R, the instrument shaft and end effector will also rotate in the direction of arrow R with the rotation of the carriage. In this configuration, the central axis of rotation of the rotatable carriage 226 coincides with the shaft 214 of the instrument 210. The illustrated embodiments depict a configuration of the instrument holder 202 allowing axial and rotational positioning of the rotatable carriage 226 with respect to the instrument holder base member 220. However, in other embodiments, any number of drive elements can be used with the instrument holder 202 to position the rotatable carriage 226 in any desired position and/or orientation.

The rotatable carriage 226 may be rotatably coupled to the carriage support 224 and manipulable by the axial and rotational drive elements 242 and 244, as described above. The rotatable carriage 226 may be configured to support and mount the medical instrument 210 on a distal end portion of the rotatable carriage 226 (i.e., away from the surgical site) and transfer actuation forces to the mounted medical instrument 210. An attached medical instrument 210 can be manipulated by the axial and rotational drive elements 242 and 244 for use during a medical procedure wherein actuation forces output by the drive elements 242 and 242 are transferred to the medical instrument 210. In this regard, change(s) in position and orientation of the rotatable carriage 226 generally correspond to the same change(s) in position and orientation of the medical instrument 210. However, portions of the medical instrument 210 may still be individually manipulated independent of the change(s) in position and orientation of the rotatable carriage 226 (e.g., articulation and/or manipulation of an end effector 216, etc.). In the illustrated embodiments, the rotatable carriage 226 is configured to change the axial position and the angular orientation of the medical instrument 210. However, the rotatable carriage 226 may be further configured to change any position and/or orientation of the medical instrument 210.

The rotatable carriage 226 may further include one or more components in mechanical, optical, and/or electrical communication with the proximal end portion of the medical instrument 210. As shown, for example, the rotatable carriage 226 may include drive elements 228 (e.g., motors or actuators) arranged within the rotatable carriage 226 to transfer mechanical movement through the distal end portion of the carriage 226 to the medical instrument 210. For example, the drive elements 228 may be configured to articulate and/or manipulate the end effector 216, among other possible movements. The drive elements 228 may be controlled by electrical signals entering the rotatable carriage 226 from a connector positioned on the rotatable carriage 226 (e.g., through a data or energy cable 340 shown in FIG. 7A), or passing through the carriage support 224 to the rotatable carriage 226. The drive elements 228 may be connected to output drive couplings to transfer articulation forces to the medical instrument 210. The rotatable carriage 226 may also include electrical and/or optical pass-through components to allow external communication with the medical instrument 210 (e.g., electric current for cauterization, light energy for an endoscope, etc.), as will be explained in greater detail below with reference to FIG. 7A.

The medical instrument 210 may include an instrument housing 212, a shaft 214, and an end effector 216. The medical instrument 210 may include a plurality of articulable degrees of freedom that can be articulated when mounted to the rotatable carriage 226. The instrument housing 212 is configured to removably couple the medical instrument 210 to the distal end portion of the rotatable carriage 226 (e.g., a proximal end portion of the instrument housing 212 may be coupled to the distal end portion of the carriage 226). The instrument housing 212 is generally configured to enclose various internal components of the medical instrument 210 (which are omitted from the figures for sake of clarity). The instrument housing 212 may include one or more force transmission input couplings on the proximal end portion (e.g., disks 229, see FIG. 2A) of the housing 212, wherein the force transmission input couplings correspond to the drive elements 228. The force transmission input couplings of the instrument 210 may be configured to receive an output from the drive elements 228 of the carriage 226, and thereby cause manipulation of the medical instrument 210. For example, one of the input couplings of the instrument 210 can be used to articulate the end effector 216 of the mounted medical instrument 210 around a first axis (e.g., pitch axis), another input coupling can be used to articulate the end effector 216 around a second axis (e.g., yaw axis) that is perpendicular to the first axis, another input coupling can be used to articulate a clamping jaw of the end effector 216, and another input coupling can be used to articulate a stapling and cutting cartridge of the end effector 216. The medical instrument 210 also may include an instrument shaft 214 extending away from the instrument housing 212 toward the distal end portion 206 of the instrument holder base member 220. The instrument shaft 214 may have the end effector 216 positioned at an end of the instrument shaft 214, and may be configured to enter the patient P through the cannula 222. The instrument shaft 214 may be configured to surround one or more of the internal components of the medical instrument 210 (e.g., cables, wires, fibers, light guides, etc.).

As described above, the rotatable carriage 226 may be rotated relative to the instrument holder base member 220 in the direction of arrow R. As the rotatable carriage 226 rotates, portions or all of the medical instrument 210 mounted to the carriage will also be rotated (e.g., in a direction corresponding to roll of the shaft 214 and the end effector 216). For example, in some embodiments, the rotation of the rotatable carriage 226 will cause the shaft 214 of the instrument to rotate in a roll direction without twisting the shaft 214 relative to other components of the medical instrument 210. In some embodiments, rotation of the carriage may cause the entire instrument to roll as a single unit. The rotation of the medical instrument 210 by the rotatable carriage 226 allows adjustable orientation in the roll DOF of the end effector 216 without twisting of the instrument shaft 214 relative to other components of the medical instrument 210. In this regard, the internal components (e.g., wires, cables, fibers, light guides, etc.) of the instrument shaft 214 do not experience the unwrap torque described above, thereby reducing tensile load on the inner wrap and/or core of the internal components of the instrument shaft 214, and extending the life of the medical instrument 210. By rolling the rotatable carriage 226 of the instrument holder 202, the internal friction of the internal components of the instrument shaft 214 is consistent such that articulation of the end effector 216 during use can be more consistently and precisely controlled by an operator O.

Figure 3A:
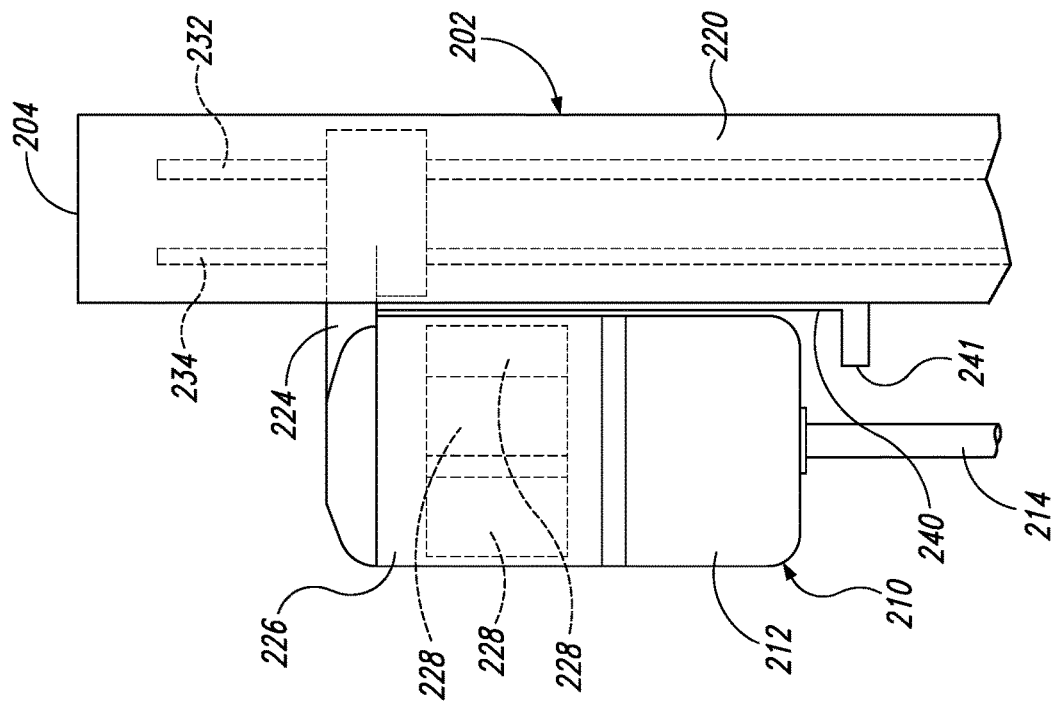
FIGS. 3A and 3B are right side elevation detail views of a portion of the instrument holder and medical instrument of FIGS. 2A and 2B, showing the instrument holder and the medical instrument in a disassembled configuration (FIG. 3A) and an assembled configuration (FIG. 3B).

During installation and removal of the medical instrument 210 to and from the proximal end portion of the rotatable carriage 226 (the patient-facing side), it may be desirable to limit the amount of travel of the medical instrument 210 in the insertion direction (i.e., in a direction toward the surgical field and the patient P), as unintended and/or excessive insertion of the instrument 210 toward the patient P can cause injury to the patient P and/or damage to the equipment of the system 100. Several examples of embodiments configured to limit the amount of insertion of the medical instrument 210 during instrument installation and removal are shown in FIGS. 3A-4, and will now be explained in greater detail. It may be further desirable to provide clocking and alignment of the medical instrument 210 with respect to the rotatable carriage 226, such as alignment of one or more electrical, mechanical, and optical connections between the medical instrument 210 and the rotatable carriage 226.

Figure 3B:
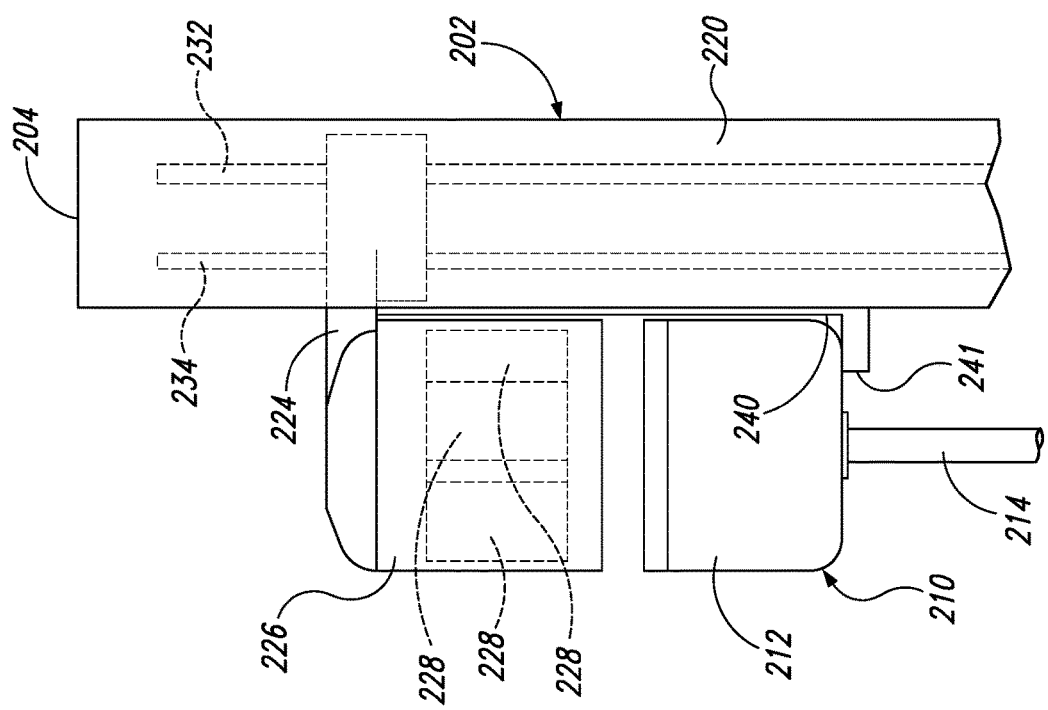
Figure 4:
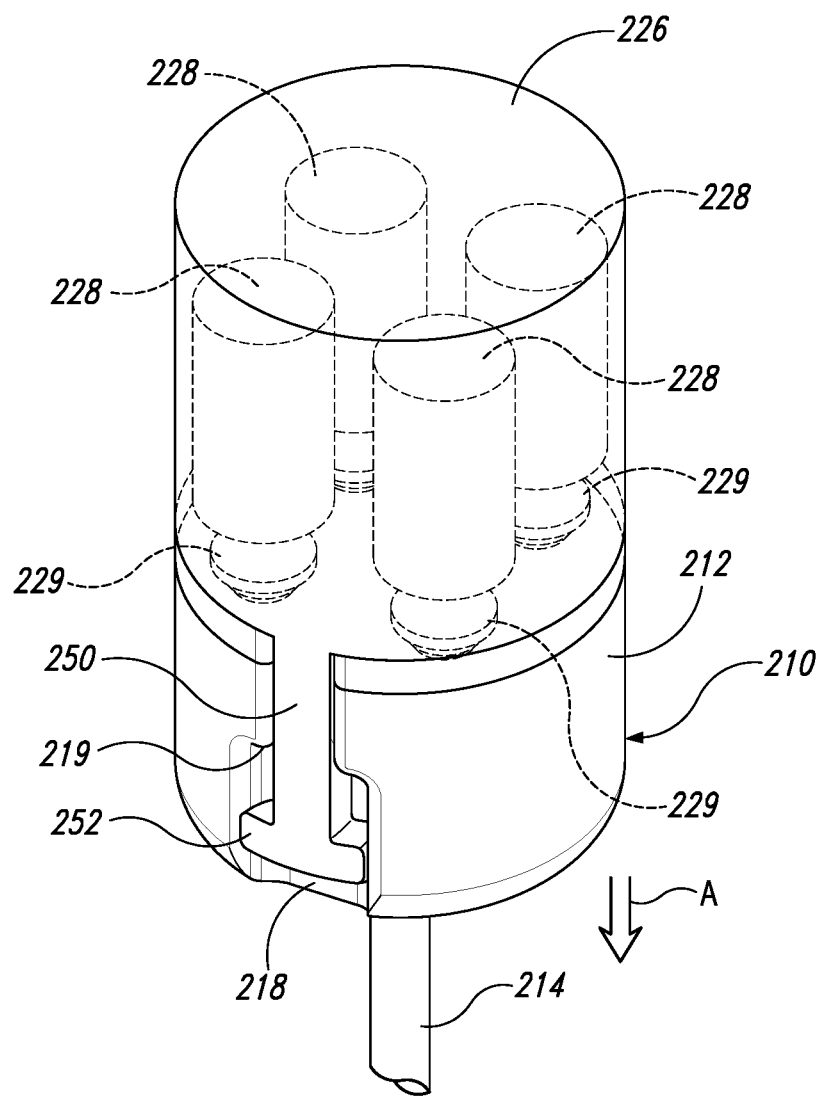
FIG. 4 is a perspective detail view of a portion of the instrument holder and medical instrument of FIGS. 2A and 2B, showing a rotatable carriage of the instrument holder and the medical instrument in an assembled configuration.

FIGS. 3A and 3B are right side elevation detail views of a portion of the instrument holder 202 and the medical instrument 210 in accordance with embodiments of the present disclosure. In particular, FIG. 3A illustrates the rotatable instrument holder 202 and the medical instrument 210 in a disassembled configuration, and FIG. 3B illustrates the instrument holder 202 and the medical instrument 210 in an assembled configuration. As shown, the carriage support 224 may include a catch 240 generally aligned with the instrument holder base member 220 and configured to interface with a lower surface of the instrument housing 212 to prevent inadvertent insertion of the medical instrument 210 toward the surgical field, e.g., into the anatomy of the patient P (not shown). The catch 240 may be coupled to the carriage support 224 such that the catch 240 travels with the carriage support 224 along the instrument holder base member 220 during axial motion of the carriage support 224. In this regard, the medical instrument 210 may be coupled and decoupled to the carriage 226 at various axial positions of the carriage support 224 relative to the instrument holder 202 without over-insertion of the instrument 210 toward the surgical field. In other embodiments, the catch 240 may be attached to the rotatable carriage 226 (see FIG. 4), attached to a sterile adapter (see, e.g., FIGS. 6A-6F), or may be a separate component.

As shown in FIG. 3A, the instrument 210 may be detached from the carriage 226 while a stop mechanically constrains the instrument 210 from being further moved towards the surgical field. For example, the instrument housing 212 can be separated from the rotatable carriage 226 and is generally allowed to travel axially away from the rotatable carriage 226 until the instrument housing 212 abuts a catch protrusion 241. The catch protrusion 241 may project away from the catch 240 and physically interfere with the axial travel of the medical instrument 210 at a specified insertion distance away from the rotatable carriage 226. The insertion compliance (e.g., the axial separation distance the medical instrument 210 can travel before contacting the catch protrusion 241) of the medical instrument 210 may be implemented based on a variety of factors, including the size of the surgical field, the procedure to be performed, the configuration of the components of the system 100, etc. Generally, the insertion compliance must be at least greater than the clearance required for aligning the medical instrument 210 to the rotatable carriage 226, for example, lateral clearance for one or more alignment features (see, e.g., FIG. 5A). When the medical instrument 210 is in the assembled configuration shown in FIG. 3B, the catch 240 may be positioned to not interfere with or impede rotation or insertion of the medical instrument 210 by the rotatable carriage 226. Optionally, in some embodiments, the position of the catch 240 relative to at least one of the carriage 226, the carriage support 224, a sterile adapter, or a mounted instrument housing 212 may be adjusted to adjust the amount of insertion compliance (e.g., to accommodate instruments with differently sized instrument housings). For example, the catch 240 may include a vertically telescoping feature that may be locked to set the amount of insertion compliance. Optionally, in some embodiments, the amount of projection of the catch protrusion 241 may be adjusted (e.g., to accommodate instruments with differently sized instrument housings). For example, the catch protrusion 241 may include a horizontally telescoping feature that may be locked to set the amount of protrusion.

FIG. 4 is a perspective detail view of a portion of the rotatable carriage 226 and the medical instrument 210 in an assembled configuration in accordance with embodiments of the present disclosure. As shown, the rotatable carriage 226 may include a catch 250 configured to interface with a recess or indentation 218 in the instrument housing 212 to prevent inadvertent insertion of the medical instrument 210 into the surgical field. The catch 250 may project as an attachment from a lower surface of the rotatable carriage 226 to an area that interfaces with corresponding features on the medical instrument 210. In some embodiments, the catch 250 may be part of a sterile adapter positioned between the rotatable carriage 226 and medical instrument 210 (e.g., the sterile adapters of FIGS. 6B-6D), and may project from the sterile adapter to interface with the medical instrument 210. In a similar manner to the catch 240 described above, the catch 250 is configured to allow separation of the medical instrument 210 from the rotatable carriage 226 in an axial direction away from the rotatable carriage 226 until a wall 219 of the indentation 218 in the instrument housing 212 abuts a catch protrusion 252 of the catch 250. As shown, the catch protrusion 252 may project in multiple directions, and may generally form a "T" shape, with the shape of the indentation 218 and the wall 219 generally having complementary features to interface with the catch protrusion(s) 252. The interface of the catch 250 with the indentation 218 may also be configured to provide a clocking alignment of the medical instrument 210 during installation of the instrument 210 to the rotatable carriage 226. In this regard, the placement of the indentation 218 can rotationally orient the instrument housing 212 to the desired clocked position, prior to attaching the instrument 210 to the rotatable carriage 226, by laterally interfacing with the catch 250 and/or the catch protrusion 252 as the medical instrument 210 is translated axially toward the rotatable carriage 226.

Upon removal of the medical instrument 210 from the rotatable carriage 226, the medical instrument 210 is configured to travel axially away from the rotatable carriage 226 in the insertion direction (as shown by the arrow A) until the catch protrusion 252 abuts the wall 219 of the indentation 218 and limits further insertion. As with the catch 240 described above, the catch 250 may be similarly configured to physically interfere with the axial travel of the medical instrument 210 at a specified insertion distance away from the rotatable carriage 226, and the specified insertion distance may be adjustable as described above with respect to catch 240. The insertion compliance (e.g., the axial distance the medical instrument 210 can travel before the wall 219 impacts the catch protrusion 252) of the medical instrument 210 may be implemented based on a variety of factors, including the size of the surgical field, the procedure to be performed, the configuration of the components of the system 100, etc. Generally, the insertion compliance must be at least greater than the clearance required for aligning the medical instrument 210 to the rotatable carriage 226, for example, lateral clearance for one or more alignment features (see, e.g., FIG. 5A).

Figure 5A:
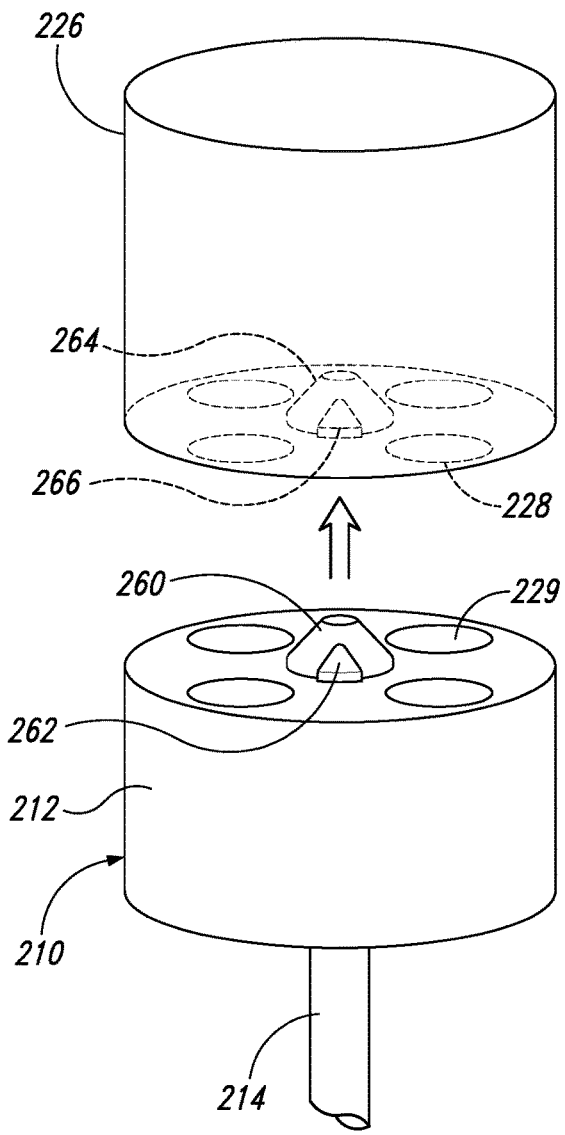
FIGS. 5A and 5B are top and bottom perspective detail views, respectively, of the rotatable carriage and medical instrument of FIGS. 2A and 2B, showing a clocking and centering alignment feature.
Figure 5B:
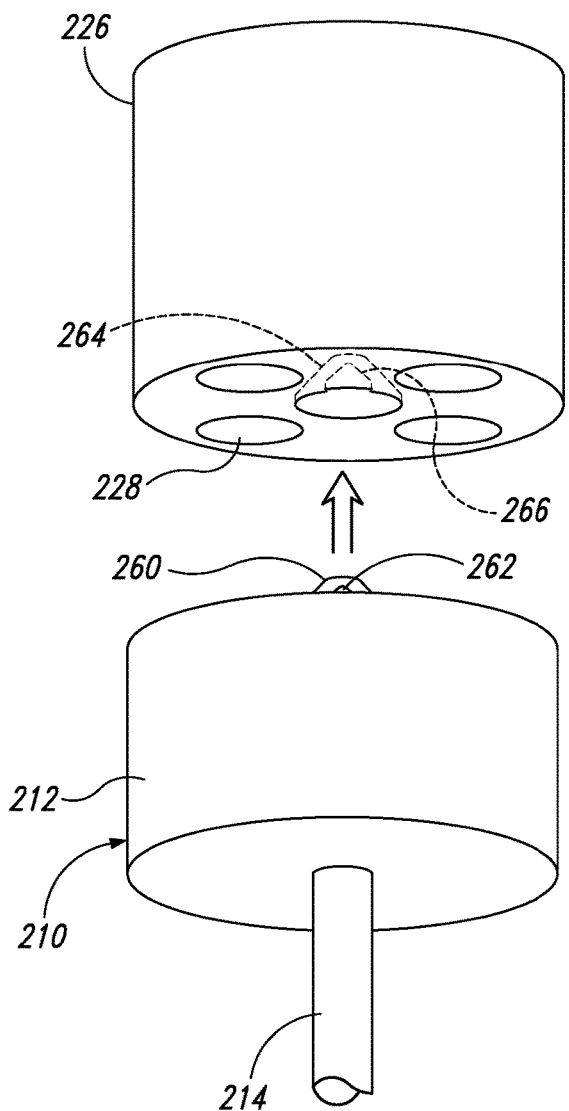

FIGS. 5A and 5B show top and bottom perspective detail views, respectively, of the rotatable carriage 226 and the medical instrument 210 having a clocking and centering alignment feature configured in accordance with embodiments of the present disclosure. The instrument housing 212 may include a male alignment projection 260 positioned and configured to align and clock the medical instrument 210 with respect to the rotatable carriage 226 and sterile adapter during installation. The male alignment projection 260, for example, may be frustoconical with a smooth upper section to provide radial alignment of the medical instrument 210 with the rotatable carriage 226. In other embodiments, however, the male alignment projection 260 may have other suitable shapes/configurations. The male alignment projection 260 may further include a clocking alignment protrusion 262 configured to provide clocking alignment of the medical instrument 210 with respect to the rotatable carriage 226, while the male alignment protrusion 260 generally provides a centering alignment of central axes of the medical instrument 210 and the rotatable carriage 226.

As shown in FIG. 5B, the rotatable carriage 226 may include a female alignment recess 264 that is generally complementary to the size and shape of the male alignment projection 260. In some embodiments, a sterile adapter between the carriage 226 and the instrument 210 (e.g., the sterile adapter of FIGS. 6B-6D) may have a similar female alignment recess as the rotatable carriage 226. The female alignment recess 264, for example, may be inverse frustoconical with surfaces configured to interface with the male alignment projection 260 and provide radial alignment of the medical instrument 210 with the rotatable carriage 226. In other embodiments, however, the female alignment recess 264 may have any other suitable shapes/configurations.

The female alignment recess 264 may further include a clocking alignment indentation 266 that generally corresponds to the clocking alignment protrusion 262 to provide clocking alignment of the medical instrument 210 with respect to the rotatable carriage 226 and/or sterile adapter. During installation of the medical instrument 210 to the rotatable carriage 226 and sterile adapter, the interface of the male alignment projection 260 and the female alignment recess 264 provide a rough centering alignment at the start of engagement, and adjust the position of the medical instrument 210 into the desired final centered alignment as the medical instrument 210 is coupled to the rotatable carriage 226. After initial engagement of the male alignment projection 260 and the female alignment recess 264, the clocking alignment protrusion 262 begins to interface with the clocking alignment indentation 266 to provide rough clocking alignment at the start of engagement, and adjust the clocked orientation of the medical instrument 210 to the desired final clocked orientation as the medical instrument 210 is coupled to the rotatable carriage 226. Although the male alignment projection 260 is shown on the medical instrument 210 and the female alignment recess 264 is shown on the rotatable carriage 226, in other embodiments the male portion is positioned on the rotatable carriage 226 with the female portion positioned on the medical instrument 210, or a combination of complementary male projections and female recesses may be positioned on each component. Optionally, in some embodiments, a plurality of projections and recesses may be provided to facilitate alignment, and may be positioned at various locations along the mating surfaces of the carriage 226 and the instrument 210.

Figure 6A:
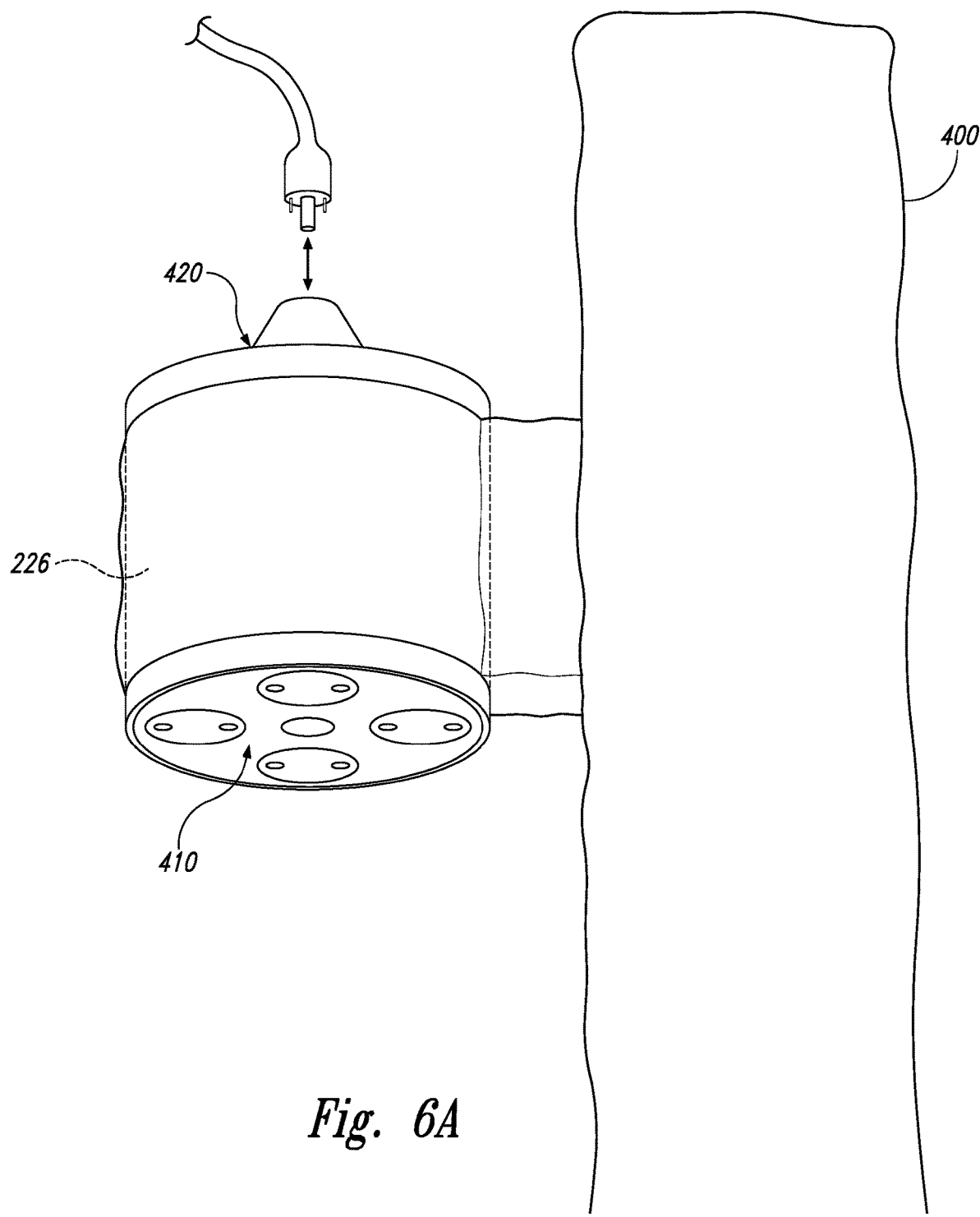
FIG. 6A is a perspective view of an instrument holder with a sterile drape.

Embodiments of a sterile drape and sterile adapter will now be described in greater detail. Referring to FIG. 6A, a sterile drape 400 is shown covering the instrument holder 202, including the instrument holder base member 220, the carriage support 224, and the rotatable carriage 226. In some embodiments, the sterile drape 400 may also cover some or all of the manipulator assembly 126 supporting the instrument holder 202, as well as the other portions of the manipulating system 121. The sterile drape 400 may be used to shield non-sterile components of the manipulator assembly 126 from the sterile field and to protect the manipulator assembly 126 from contaminants during a surgical procedure.

As shown in FIG. 6A, the sterile drape 400 may include a sterile adapter 410 (e.g., a distal sterile adapter) positionable at a distal end portion of the rotatable carriage 226 to provide an interface between the rotatable carriage 226 and a mounted instrument 210. The sterile drape 400 may also include a sterile adapter 420 (e.g., a proximal sterile adapter) positionable at a proximal end portion of the rotatable carriage 226 to provide an interface between the rotatable carriage 226 and a proximally mounted element, such as the data or energy cable 340, described below. When sterile adapters 410 and 420 are mounted to the rotatable carriage 226, an exterior of the sterile adapters 410 and 420 faces the surgical environment while an interior of the sterile adapters 410 and 420 faces the rotatable carriage 226. As described in further detail below, the sterile adapters 410 and 420 allow for mechanical and electrical signals and energy to be transferred between a non-sterile manipulator assembly 126 and a medical instrument 210 and/or data or the energy cable 340 positioned in the sterile field, while permitting movement of the instrument holder 202 and the manipulator assembly 126, such as rotation of the rotatable carriage 226. The sterile adapters 410 and 420 may be made of a rigid material, such as polycarbonate, acrylonitrile butadiene styrene (ABS), any suitable thermoplastic or thermoset materials, or the like. In some embodiments, the sterile adapters 410 and 420 may be spaced apart with drape material 430 positioned between the sterile adapters 410 and 420 and surrounding the rotatable carriage 226. In other embodiments, the sterile adapters 410 and 1020 may be part of an enclosure (e.g., a rigid enclosure) that surrounds the rotatable carriage 226.

Figure 6B:
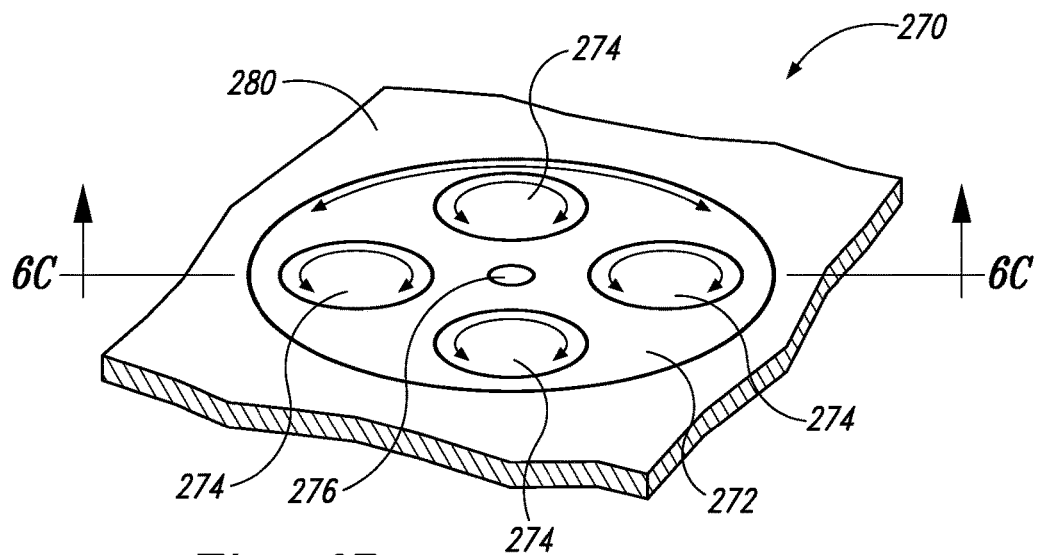
FIGS. 6B and 6C are perspective and cross-sectional views, respectively, of a nested disk sterile adapter
Figure 6C:
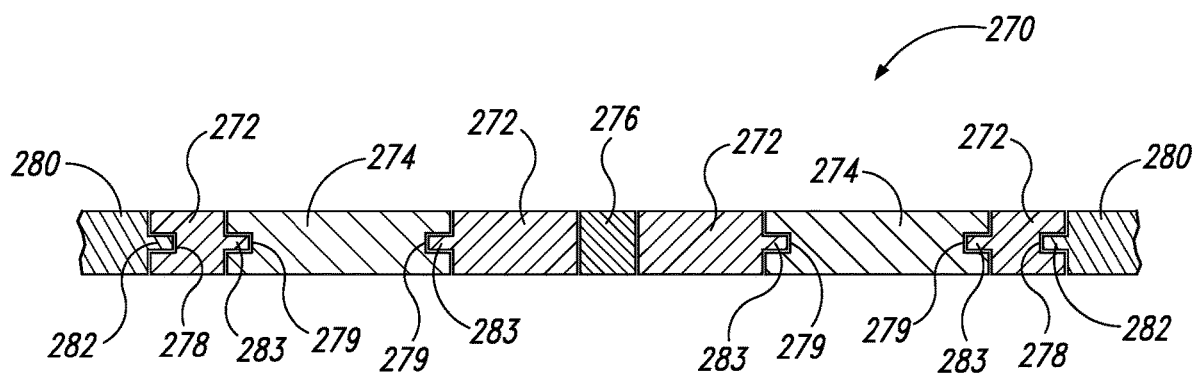
Figure 6D:
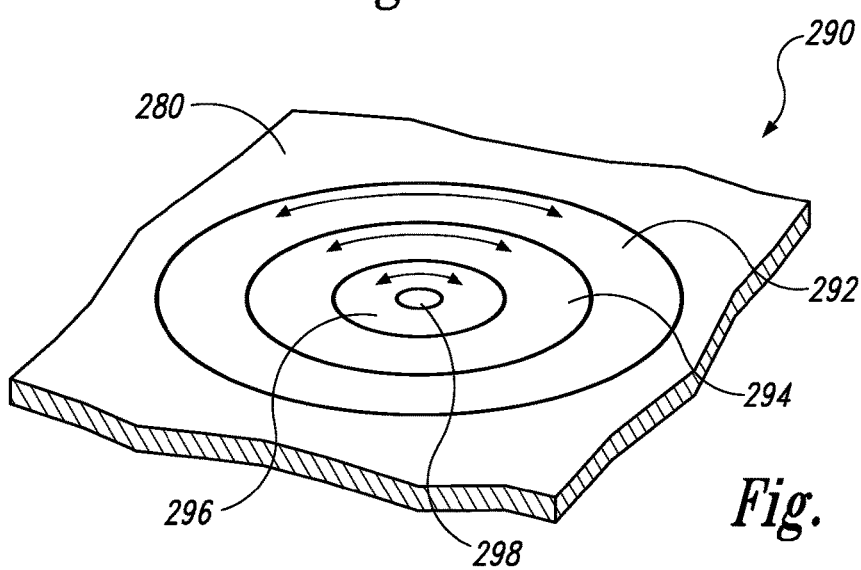
FIG. 6D is a perspective view of another nested disk sterile adapter, the nested disk sterile adapters configured in accordance with embodiments of the present disclosure.

FIGS. 6B-6D are perspective and cross-sectional views of embodiments of nested disk sterile adapters configured in accordance with embodiments of the present disclosure. The sterile adapters of FIGS. 6B-6D are examples of the distal sterile adapter 410. Referring initially to FIGS. 6B and 6C, a nested disk sterile adapter 270 may be configured for positioning between the rotatable carriage 226 and the medical instrument 210 (e.g., in the gap between the rotatable carriage 226 and the medical instrument 210 in FIG. 3A) to provide a barrier between sterile and nonsterile environments in the patient coordinate space 120. The nested disk sterile adapter 270 may include a frame 280, a roll disk 272 configured to rotate with respect to the frame 280, and a plurality of inner disks 274 configured to rotate with respect to the roll disk 272. The inner disks 274 may align with output disks of the motors 228 of the rotatable carriage 226 and the disks 229 on the medical instrument 210. When installed, the nested disk sterile adapter 270 may be configured to transfer mechanical movement of the motors 228 to the medical instrument 210. The nested disk sterile adapter 270 may further include a light pipe 276 (e.g., an optical window) centered on the roll disk 272 and configured to allow light to pass through from the rotatable carriage 226 to the medical instrument 210. In other embodiments, one or more electrical connections may pass through the nested disk sterile adapter 270 to transmit electrical signals between the rotatable carriage 226 and the medical instrument 210.

The frame 280 of the sterile adapter 270 may extend laterally away from the roll disk 272 to any suitable distance to create the desired barrier between the sterile and nonsterile environments. The frame 280 may include drape geometry (not shown) and/or have a drape material extending away from the frame 280 and configured to further extend the sterile barrier as needed away from the sterile adapter, e.g., for various medical procedures, patient anatomy, the configuration of system 100, etc. As shown in FIG. 6C, the frame 280 may interface with the perimeter of the roll disk 272 using a complementary protrusion and recess geometry, e.g., having a male protrusion 278 extending into a female recess 282. In other embodiments, the male protrusion is positioned instead on the perimeter of the roll disk 272 and configured to extend into a female recess on the frame 280. In the illustrated configuration, the overlap of the protrusion 278 with the recess 282 can prevent contaminants, fluids, and other debris from traveling across the sterile barrier. Similarly, the roll disk 272 may interface with the perimeter of the inner disks 274 using a complementary protrusion and recess geometry, e.g., having a male protrusion 283 extending into a female recess 279. In other embodiments, the male protrusion is positioned instead on the perimeter of the inner disks 274 and configured to extend into a female recess on the roll disk 272. In the illustrated configuration, the overlap of the protrusion 283 with the recesses 279 can prevent contaminants, fluids, and other debris from traveling across the sterile barrier. Other suitable sterile interfaces between the frame 280, the roll disk 272, and the inner disks 274 are also within the scope of the present disclosure.

FIG. 6D is a perspective view of another embodiment of a nested disk sterile adapter 290 configured for positioning between the rotatable carriage 226 and the medical instrument 210 to provide a barrier between sterile and nonsterile environments in the patient coordinate space 120. The nested disk sterile adapter 290 may include the frame 280, and a plurality of concentric disks 292, 294, and 296, each of the disks being independently rotatable with respect to each other and the frame 280. The concentric disks 292, 294, and 296 may be configured to transfer mechanical movement of actuators of the rotatable carriage 226 to the medical instrument 210. The nested disk sterile adapter 290 may include similar protrusion and recess geometry as described above with respect to the nested disk sterile adapter 270. Such protrusion and recess geometry may be positioned between the frame 280 and each of the concentric disks 292, 294, and 296. The nested disk sterile adapter 290 may further include a central light pipe 298 through the innermost concentric disk 296 and configured to allow light energy to pass through from the rotatable carriage 226 to the medical instrument 210. In other embodiments, one or more electrical connections may pass through the nested disk sterile adapter 290 to transmit electricity between the rotatable carriage 226 and the medical instrument 210.

Figure 6E:
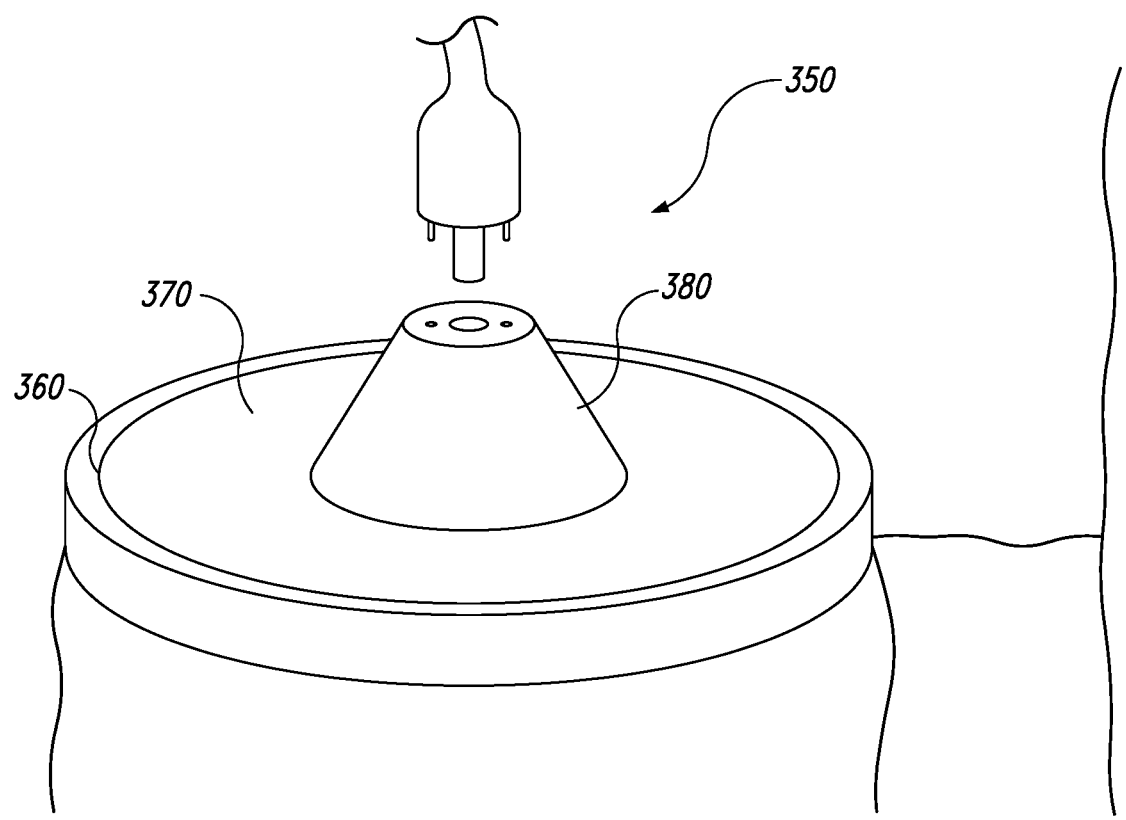
FIGS. 6E and 6F are perspective and cross-sectional views, respectively, of another sterile adapter.
Figure 6F:
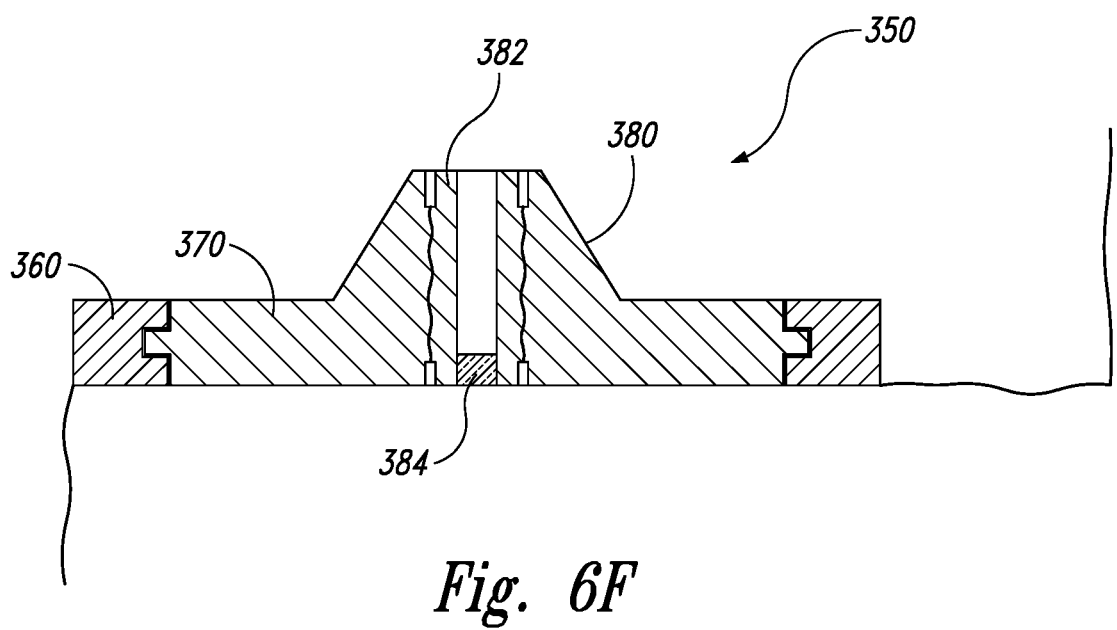

FIGS. 6E-6F are perspective and cross-sectional views of embodiments of another sterile adapter 350 configured in accordance with embodiments of the present disclosure. The sterile adapter 350 of FIGS. 6E-6F are examples of the proximal sterile adapter 420. The sterile adapter 350 may be configured for positioning between a proximal end portion of the rotatable carriage 326 and a proximally mounted element, such as the data or energy cable 340 described below (see FIG. 7A). The sterile adapter 350 provides a barrier between sterile and nonsterile environments in the patient coordinate space 120, while permitting mechanical and electrical signals and energy to be transferred between the manipulator assembly 126 and the data or energy cable 340 positioned in the sterile field and also permitting movement of the instrument holder 202.

The sterile adapter 350 may include a frame 360, a roll disk 370 configured to rotate with respect to the frame 360, and a connector 380 configured to mate to the data or energy cable 340. The connector 380 may be rotatable along with the rotation of the roll disk 370. The connector 380 may include an electrical conductor 382 configured to allow electricity (e.g., signals, data, and/or power) to be transmitted through the sterile adapter 350. The electrical conductor 382 may be in electrical contact with an electrical connector 331 (see FIG. 7A) of the carriage 326 and with connector features of the data or energy cable 340, to allow the electrical signals, data, and/or power to be communicated between the data or energy cable 340 and the medical instrument 310 positioned at the distal end portion of the rotatable carriage 326. The connector 380 may further include a light pipe 384 (e.g., an optical window) centered on the sterile adapter 350 and configured to allow light to pass through the sterile adapter 350. The light pipe 384 may be in communication with a light pipe 327 of the rotatable carriage 326 (see FIG. 7A), such that light and communication signals may be transmitted between the data or energy cable 340 and the medical instrument 310 positioned at the distal end portion of the rotatable carriage 326. In some embodiments, the electrical conductor 382 may be positioned radially outward relative to the light pipe 384. In some embodiments, the sterile adapter 350 may include the electrical conductor 382 and not include the light pipe 384. In other embodiments, the sterile adapter 350 may include the light pipe 384 and not include the electrical conductor 382.

Figure 7B:
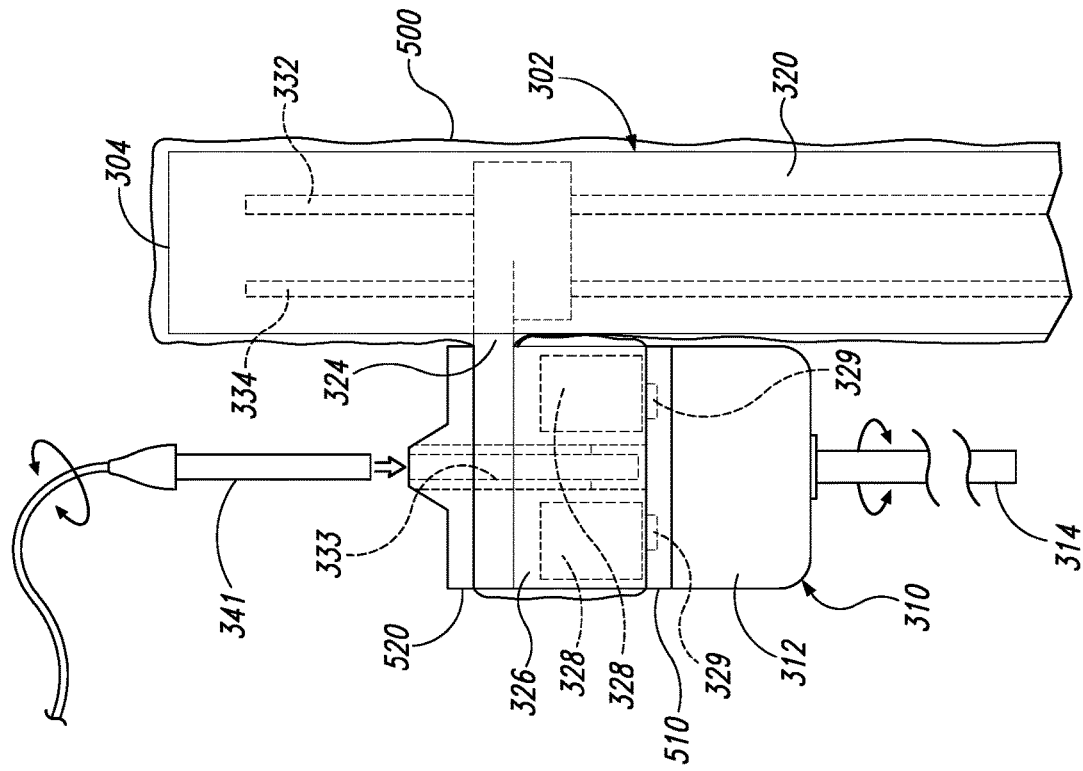
FIGS. 7A and 7B are right side elevation detail views of a portion of an instrument holder and a medical instrument configured in accordance with embodiments of the present disclosure.
Figure 7A:
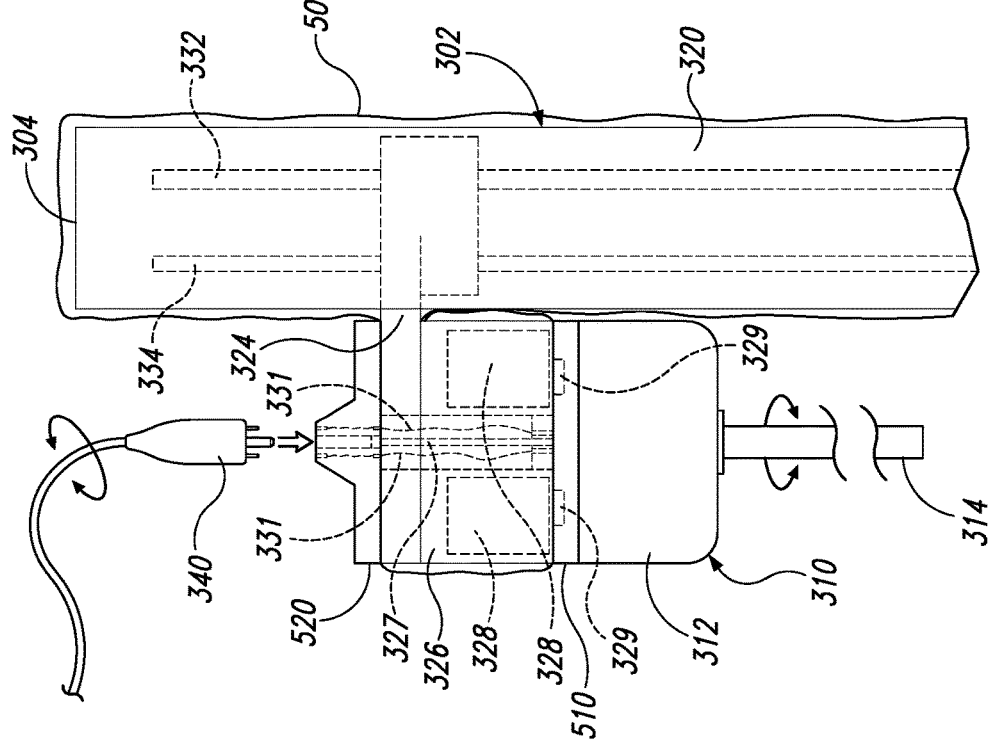

FIGS. 7A and 7B are right side elevation detail views of an instrument holder 302 and a medical instrument 310 configured in accordance with additional embodiments of the present disclosure. The instrument holder 302 and medical instrument can be used with the system 100 or other suitable systems. The instrument holder 302 can include a rotatable carriage 326. Certain features of the instrument holder 302 and the medical instrument 310 shown in FIGS. 7A and 7B are similar to features of the instrument holder 202 and the medical instrument 210 of FIGS. 2A-5B, described above. As such, the features of the instrument holder 302 and the medical instrument 310 are denoted in the 300-series with like numbers corresponding to similar features of the rotatable instrument holder 202 and the medical instrument 210 denoted in the 200-series, unless otherwise stated.

As shown in FIG. 7A, the rotatable carriage 326 may include a light guide or light pipe 327 configured to allow light (e.g., for an endoscope or fiber optic communication) to pass through the rotatable carriage 326. FIG. 7A additionally includes a drape 500 having a distal sterile adapter 510 and a proximal sterile adapter 520. The distal sterile adapter 510 may be similar to the sterile adapters 270 or 290 described above, and the proximal sterile adapter 520 may be similar to the sterile adapter 350 described above. As shown in FIG. 7A, the light pipe 327 of the rotatable carriage 326 is aligned with the light pipe of the distal sterile adapter 510 and the light pipe of the proximal sterile adapter 520. This allows light and/or communication signals to be transmitted between a data or energy cable connected to the proximal end portion of the rotatable carriage 326 and a medical instrument 310 (e.g., a 0° endoscope, as shown in FIG. 7A, etc.) connected to the distal end portion of the rotatable carriage 326. The rotatable carriage 326 may further include an electrical conductor 331 extending through the rotatable carriage 326 and may be positioned radially outward of the light pipe 327. As further shown in FIG. 7A, the electrical conductor 331 of the rotatable carriage 326 is in contact with the electrical conductor of the distal sterile adapter 510 and the electrical conductor of the proximal sterile adapter 520. The electrical conductor 331 of the rotatable carriage 326 in conjunction with the electrical connectors of the sterile adapters 510 and 520 may be configured to transmit electricity (e.g., signals, data, and/or power) between the data or energy cable 340 connection on the proximal end portion of the rotatable carriage 326 and a shaft 314 of the medical instrument 310 at the distal end portion of the rotatable carriage 326. The electrical connectors of the sterile adapters 510 and 520, and/or the data or energy cable 340 may have connector features (e.g., pogo pins, not shown) to allow electrical communication during rotation of the rotatable carriage 326. In some embodiments, the light pipe 327 may be surrounded by a faraday cage (not shown) to protect data signals passing through the rotatable carriage 326 from interference. Although shown as an endoscope in FIG. 7A, in other embodiments, the medical instrument 310 is any suitable medical instrument, e.g., an articulable end effector, an electrocautery device, etc.

FIG. 7B shows another embodiment of the rotatable carriage 326 including a central bore 333, with the light pipe 327 of the embodiment of FIG. 7A removed. FIG. 7B additionally includes the drape 500 having the distal sterile adapter 510 and a proximal sterile adapter 530. The distal sterile adapter 510 may be similar to the sterile adapters 270 or 290 described above. The proximal sterile adapter 530 has a portion that is insertable into the central bore 333. The proximal sterile adapter 530 and the central bore 333 are configured to allow a data or energy cable 341 to be inserted through the rotatable carriage 326 and provide communication signals to the medical instrument 310 (e.g., a 0° endoscope, as shown in FIG. 7B, etc.) through a sterile adapter (e.g., a nested disk sterile adapter shown in FIGS. 6B and 6D, etc.). In this regard, the data or energy cable 341 may include one or more cable types, e.g., a light pipe, optical fibers, coaxial conductors, copper conductors, twisted wire pairs, etc.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present disclosure. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An apparatus, comprising:
  a carriage and a carriage support, wherein:
    the carriage comprises a proximal end portion, a distal end portion, and a longitudinal axis extending between the proximal end portion and the distal end portion, the longitudinal axis defining an axis of rotation of the carriage,
    the carriage is coupled with and rotatable relative to the carriage support, and
    the carriage is configured to removably couple an instrument to the carriage;
  a light pipe extending axially through the carriage and configured to transmit light energy between the proximal end portion and the distal end portion of the carriage and toward the instrument in a coupled state of the instrument to the carriage; and
  an electrical conductor extending through the carriage radially outward of the light pipe, wherein the electrical conductor is configured to transmit electricity between the proximal end portion and the distal end portion of the carriage and toward the instrument in a coupled state of the instrument to the carriage.

2. The apparatus of claim 1, further comprising an instrument holder comprising an instrument holder base member, wherein the carriage support and carriage are configured to translate relative to the instrument holder base member.

3. The apparatus of claim 1, wherein rotation of the carriage about the longitudinal axis causes a roll of the instrument in a coupled state of the instrument to the carriage.

4. The apparatus of claim 1, wherein the distal end portion of the carriage is configured to removably couple to a proximal end portion of the instrument, wherein the distal end portion of the carriage is configured to be positioned between a surgical field and the proximal end portion of the carriage, and wherein the carriage comprises at least one drive element configured to articulate the instrument.

5. The apparatus of claim 4, further comprising a sterile adapter positioned between the carriage and the instrument, wherein the sterile adapter is configured to transmit mechanical movement, light energy, and/or electricity between the carriage and the instrument.

6. The apparatus of claim 5, wherein the sterile adapter further comprises a catch projecting axially away from the distal end portion of the carriage, and wherein the catch has a catch protrusion configured to limit an axial separation distance of the instrument from the carriage.

7. The apparatus of claim 4, further comprising a sterile adapter positioned at the proximal end portion of the carriage, wherein the sterile adapter is configured to transmit mechanical movement, light energy, and/or electricity between a connector and the carriage.

8. The apparatus of claim 4, further comprising:
  an alignment projection extending outwardly from one of the distal end portion of the carriage and the proximal end portion of the instrument; and
  an alignment recess extending into the other of the distal end portion of the carriage and the proximal end portion of the instrument,
  wherein the alignment projection has a shape corresponding to a shape of the alignment recess to bring the carriage and the instrument into alignment in a lateral direction.

9. The apparatus of claim 8, further comprising:
a clocking projection extending outwardly from the alignment projection; and
a clocking recess extending into the alignment recess,
wherein the clocking projection has a shape corresponding to a shape of the clocking recess to orient the instrument and the carriage into a clocked position.

10. The apparatus of claim 1, wherein the light pipe is coupled to a cable configured to connect to the proximal end portion of the carriage and transmit electricity to the electrical conductor and light energy to the instrument.

11. The apparatus of claim 1, wherein the electrical conductor is configured to transmit one or more of data and power to the instrument.

12. The apparatus of claim 2, further comprising:
an axial drive element operably coupled to a transmission member extending to the carriage support; and
a rotational drive element operably coupled to a transmission member extending to the carriage support,
wherein the axial drive element is configured to drive translation of the carriage support so as to axially position the carriage support with respect to the instrument holder base member, and wherein the rotational drive element is configured to drive rotation of the carriage about the longitudinal axis so as to angularly position the carriage with respect to the instrument holder base member.

13. The apparatus of claim 1, wherein the carriage further comprises a catch projecting axially away from the distal end portion of the carriage, and wherein the catch has a catch protrusion configured to limit an axial separation distance of the instrument from the carriage.

14. The apparatus of claim 13, wherein the instrument comprises an indentation configured to interface with the catch to rotationally orient the instrument with respect to the carriage, and wherein the indentation has a wall configured to interface with the catch protrusion to limit the axial separation distance of the instrument from the carriage.

* * * * *